United States Patent
Brockway et al.

(10) Patent No.: US 8,630,716 B2
(45) Date of Patent: Jan. 14, 2014

(54) SYSTEMS AND METHODS FOR PROVIDING NEURAL STIMULATION TRANSITIONS

(75) Inventors: Marina V. Brockway, Shoreview, MN (US); Paul A. Haefner, Circle Pines, MN (US); Anthony V. Caparso, San Jose, CA (US); Wondimeneh Tesfayesus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/587,654

(22) Filed: Aug. 16, 2012

(65) Prior Publication Data

US 2012/0310304 A1 Dec. 6, 2012

Related U.S. Application Data

(63) Continuation of application No. 11/779,764, filed on Jul. 18, 2007, now Pat. No. 8,249,717.

(51) Int. Cl.
*A61N 1/00* (2006.01)

(52) U.S. Cl.
USPC .................................. 607/59; 607/5; 607/45

(58) Field of Classification Search
USPC ................................................. 607/5, 45, 59
See application file for complete search history.

(56) References Cited

U.S. PATENT DOCUMENTS

| | | | |
|---|---|---|---|
| 4,562,841 A | 1/1986 | Brockway et al. |
| 4,938,223 A | 7/1990 | Charters et al. |
| 5,222,494 A | 6/1993 | Baker, Jr. |
| 5,735,887 A | 4/1998 | Barreras, Sr. et al. |
| 6,099,479 A | 8/2000 | Christopherson et al. |
| 6,104,956 A | 8/2000 | Naritoku et al. |
| 6,662,052 B1 | 12/2003 | Sarwal et al. |
| 6,668,191 B1 | 12/2003 | Boveja |
| 6,760,626 B1 | 7/2004 | Boveja |
| 7,076,307 B2 | 7/2006 | Boveja et al. |
| 7,277,761 B2 | 10/2007 | Shelchuk |
| 2003/0074037 A1 | 4/2003 | Moore et al. |
| 2005/0065575 A1 | 3/2005 | Dobak |
| 2005/0131467 A1 | 6/2005 | Boveja |
| 2005/0278001 A1 | 12/2005 | Qin et al. |
| 2007/0097593 A1 | 5/2007 | Armstrong |
| 2007/0203521 A1 | 8/2007 | Dobak et al. |
| 2009/0024186 A1 | 1/2009 | Brockway et al. |

OTHER PUBLICATIONS

U.S. Appl. No. 11/779,764 Final Office Action mailed Oct. 15, 2010, 12 pgs.

(Continued)

*Primary Examiner* — Nicole F Lavert
(74) *Attorney, Agent, or Firm* — Schwegman Lundberg & Woessner, P.A.

(57) ABSTRACT

A method embodiment comprises generating a neural stimulation signal for a neural stimulation therapy. The signal is generated during a duty cycle of a stimulation period to provide the neural stimulation therapy with an intensity at a therapy level for a portion of the duty cycle. In various embodiments, a ramp up protocol is implemented to begin the duty cycle, a ramp down protocol is implemented to end the duty cycle, or both the ramp up protocol and the ramp down protocol are implemented. The ramp up protocol includes ramping up the intensity from a non-zero first subthreshold level for the neural stimulation therapy at the beginning of the duty cycle to the therapy level. The ramp down protocol includes ramping down the intensity from the therapy intensity level to a non-zero second subthreshold level for the neural stimulation therapy at the end of the duty cycle.

20 Claims, 9 Drawing Sheets

(56) References Cited

OTHER PUBLICATIONS

U.S. Appl. No. 11/779,764, Advisory Action mailed Feb. 28, 2011, 3 pgs.
U.S. Appl. No. 11/779,764, Non-Final Office Action mailed Apr. 12, 2010, 9 pgs.
U.S. Appl. No. 11/779,764, Notice of Allowance mailed Apr. 25, 2012, 7 pgs.
U.S. Appl. No. 11/779,764, Response filed Mar. 15, 2011 to Final Office Action mailed Oct. 15, 2010 and Advisory Action mailed Feb. 28, 2011, 22 pgs.
U.S. Appl. No. 11/779,764, Response filed Jan. 18, 2011 to Final Office Action mailed Oct. 15, 2010, 18 pgs.
U.S. Appl. No. 11/779,764, Response filed Jul. 12, 2010 to Non Final Office Action mailed Apr. 12, 2010, 14 pgs.
"Physician's Manual NeuroCybernetic Prosthesis System", Cyberonics 26-0006-0900/1 U.S. Domestic Version, NCP(r) Pulse Generator—Models 100 and 101, (Aug. 2002), 92 pgs.

SYSTEMS AND METHODS FOR PROVIDING NEURAL STIMULATION TRANSITIONS

CLAIM OF PRIORITY

This application is a continuation of and claims the benefit of priority under 35 U.S.C. §120 to U.S. patent application Ser. No. 11/779,764, filed on Jul. 18, 2007, now issued as U.S. Pat. No. 8,249,717, which is hereby incorporated by reference herein in its entirety.

TECHNICAL FIELD

This application relates generally to medical devices and, more particularly, to systems, devices and methods for delivering neural stimulation.

BACKGROUND

Neural stimulation has been proposed as a therapy for a number of conditions. Examples of neural stimulation therapies include neural stimulation therapies for respiratory problems such a sleep disordered breathing, blood pressure control such as to treat hypertension, cardiac rhythm management, myocardial infarction and ischemia, heart failure, epilepsy, depression, pain, migraines, eating disorders and obesity, and movement disorders. Neural stimulation therapies can involve intermittent neural stimulation.

SUMMARY

An embodiment relates to a method that comprises generating a neural stimulation signal for a neural stimulation therapy. The neural stimulation signal is generated during a duty cycle of a stimulation period to provide the neural stimulation therapy with an intensity at a therapy level for a portion of the duty cycle. In some embodiments, a ramp up protocol is implemented to begin the duty cycle. The ramp up protocol can be used to avoid or reduce overshoot in a desired response to the neural stimulation. In some embodiments, a ramp down protocol is implemented to end the duty cycle. The ramp down protocol can be used to avoid or reduce a rebound neural response. In some embodiments, both the ramp up protocol to begin the duty cycle and the ramp down protocol to end the duty cycle are implemented. The ramp up protocol includes ramping up the intensity from a non-zero first subthreshold level for the neural stimulation therapy at the beginning of the duty cycle to the therapy level. The ramp down protocol includes ramping down the intensity from the therapy intensity level to a non-zero second subthreshold level for the neural stimulation therapy at the end of the duty cycle.

An embodiment relates to a method for operating an implantable neural stimulator with programmable parameters adapted to be programmed using a patient-external device. According to various embodiments of the method, at least one ramp parameter for neural stimulation intensity is programmed using the patient-external device. A neural stimulation signal for a neural stimulation therapy is generated. The neural stimulation signal is generated during a duty cycle of a stimulation period to provide the neural stimulation therapy with an intensity at a therapy level for a portion of the duty cycle. A ramp up protocol, a ramp down protocol, or both a ramp up and ramp down protocol are implemented. The ramp up protocol has at least one programmable ramp up parameter to begin the duty cycle. The programmable ramp up parameter includes a first subthreshold level parameter for the neural stimulation therapy at the beginning of the duty cycle from which to ramp up to the therapy level, or a ramp up duration parameter, or both the first subthreshold level parameter and the ramp up duration parameter. The ramp down protocol has programmable ramp down parameters to end the duty cycle. The programmable ramp down parameter includes a second subthreshold level parameter for the neural stimulation therapy at the end of the duty cycle to which to ramp down from the therapy level, or a ramp down duration parameter, or both the second subthreshold level parameter and the ramp down duration parameter.

An embodiment relates to a method for delivering neural stimulation to a neural target of a patient. According to various embodiments, a neural stimulation signal is generated for a neural stimulation therapy. The neural stimulation signal is generated during a duty cycle of a stimulation period to provide the neural stimulation therapy with an intensity at a therapy level for a portion of the duty cycle. A ramp up protocol to begin the duty cycle or a ramp down protocol to end the duty cycle is implemented, or both the ramp up protocol to begin the duty cycle and the ramp down protocol to end the duty cycle are implemented. A physiologic response to the end of the duty cycle is monitored. The ramp up protocol, the ramp down protocol, or both the ramp up protocol and ramp down protocol are adjusted using the monitored physiologic response to the end of the duty cycle.

A neural stimulator embodiment comprises a neural stimulation delivery system and a controller. The neural stimulation delivery system is adapted to generate a neural stimulation signal for a neural stimulation therapy. The controller is adapted to control the neural stimulation delivery system to generate the neural stimulation signal during a duty cycle of a stimulation period to provide the neural stimulation therapy with an intensity at a therapy level for a portion of the duty cycle, and implement a protocol. Some embodiments implement a ramp up protocol to begin the duty cycle by ramping up the intensity from a non-zero first subthreshold level for the neural stimulation therapy at the beginning of the duty cycle to the therapy level. Some embodiments implement a ramp down protocol to end the duty cycle by ramping down the intensity from the therapy intensity level to a non-zero second subthreshold level for the neural stimulation therapy at the end of the duty cycle. Some embodiments implement a protocol that includes both the ramp up protocol to begin the duty cycle and the ramp down protocol to end the duty cycle.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
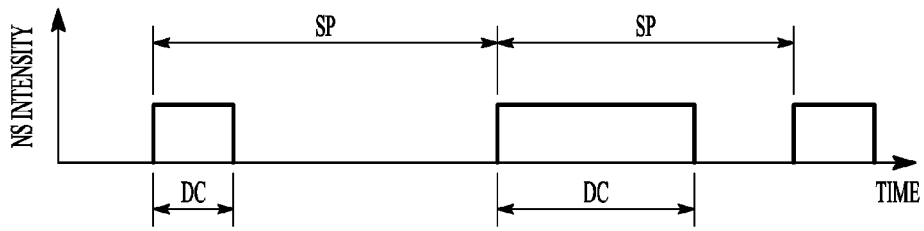
FIGS. 1 and 2 illustrate intermittent neural stimulation.
Figure 2:
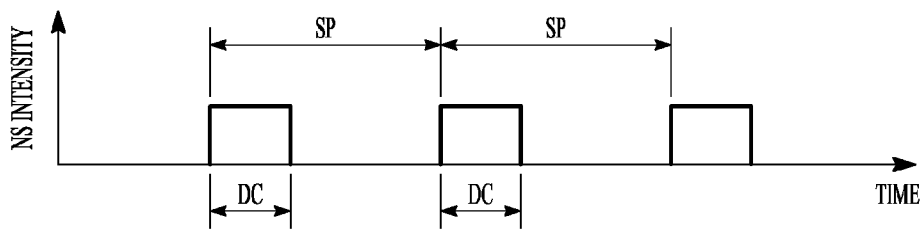

The present subject matter relates to neural stimulation therapy (NST) that includes intermittent neural stimulation. Intermittent neural stimulation can be delivered using a duty cycle of a stimulation period. FIGS. 1 and 2 illustrate intermittent neural stimulation, plotting neural stimulation intensity against time. The neural stimulation intensity is illustrated with a step function. FIG. 1 illustrates variable stimulation periods (SP) and duty cycles (DC), and FIG. 2 illustrates constant stimulation periods (SP) and duty cycles (DC). The duty cycle and stimulation period need not be constant throughout the NST. For example, the duration or frequency of the duty cycle can be adjusted to adjust an intensity of the NST. Also, the start and/or stop of the duty cycle can be dependent on enabling conditions. The duty cycle and/or stimulation period can be adjusted in every subsequent stimulation period. Unless expressly disclosed otherwise herein, "stimulation period" and "duty cycle" are not intended to only encompass constant values that result in neural stimulation in a precise periodic manner (e.g. FIG. 2), but rather is intended to include intermittent neural stimulation where therapeutically-effective or prophylactically-effective neural stimulation is delivered for a time and then not delivered for a time, and then delivered for a time, such as illustrated in FIG. 1.

The neural stimulation delivered during the duty cycle can be delivered using a variety of neural stimulation techniques, such as stimulation that uses electrical, ultrasound, thermal, magnetic, light or mechanical energy. Electrical neural stimulation is used in this document as an example of neural stimulation. In electrical stimulation, for example, a train of neural stimulation pulses (current or voltage) can be delivered during a duty cycle of stimulation. Stimulation waveforms can be square pulses or other morphologies. The stimulation pulses can be monophasic or biphasic pulses.

When a neural stimulation therapy is delivered with a step up to the therapeutic intensity at the beginning of a duty cycle, and a step down at the end of the duty cycle, transients have been observed in the neurological system. For example, abrupt changes in parasympathetic neural stimulation intensity can result in a sympathetic tone rebound. Embodiments of the present subject matter gradually increase the neural stimulation intensity at the start of stimulation train and/or gradually reduce neural stimulation intensity at the end of the stimulating train to avoid transients in the neurological system.

For example, upon conclusion of a stimulation pulse train that elicits a parasympathetic response, there is sympathetic tone rebound that is reflected in an increased heart rate and an increased mean blood pressure. One potentially harmful effect is that a disproportionate amount of sympathetic tone is activated with every duty cycle. Another potentially harmful effect is that the rapid acceleration of the heart rate, which can be observed at the end of the duty cycle of parasympathetic stimulation when the neural stimulation is abruptly turned off, can be pro-arrhythmic to a diseased heart.

An abrupt increase of stimulation at the beginning of a duty cycle can also cause a harmful transient in the neural system and lead to overshoot in response. Canine studies have indicated a sympathetic tone rebound upon conclusion of VST pulse train, as demonstrated by an abrupt heart rate increase from 34 to 112.5 bpm and an abrupt mean arterial pressure increase from 110 to 135 mmHg. Canine studies have also indicated an overshoot in parasympathetic response at the beginning of VST. Possible mechanisms involved with the observed rebound may include the activation of the baroreflex and/or chemoreflex.

Figure 3:
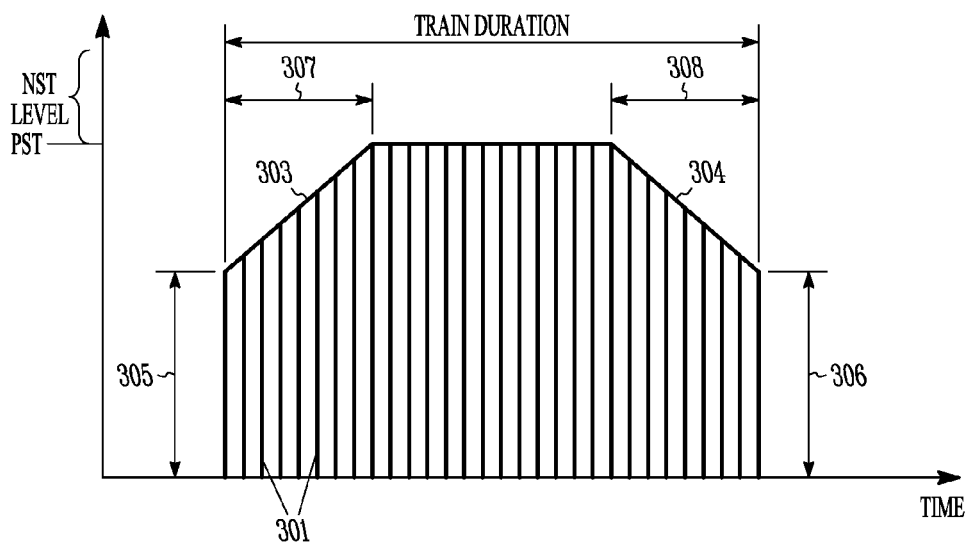
FIG. 3 illustrates a duty cycle, also referred to as a stimulation train, according to various embodiments of the present subject matter.

FIG. 3 illustrates a duty cycle, also referred to as a stimulation train, according to various embodiments of the present subject matter. The envelope of the duty cycle represents the intensity of the neural stimulation. In the illustrated embodiment, the duty cycle includes a number of stimulation pulses, represented by the vertical lines 301. The stimulation within each pulse has a frequency and an amplitude. In the illustrated example, the amplitude of the stimulation is used to adjust the stimulation intensity, in which an increase of amplitude corresponds to an increase in stimulation intensity. Those of ordinary skill in the art will understand that other parameters can be adjusted to adjust the stimulation intensity, such as the frequency of the stimulation during each pulse. The beginning of the illustrated neural stimulation train or duty cycle includes a ramp up protocol 303, and the end of the illustrated neural stimulation train includes a ramp down protocol 304.

At least a portion of the duty cycle provides stimulation at an intensity level (NST LEVEL) for the neural stimulation therapy (e.g. at or above a threshold). The duty cycle in FIG. 3 illustrates a parasympathetic stimulation threshold (PST), where the NST level is at or above the PST. Levels below the threshold level are referred to as subthreshold levels or values.

Figure 4:
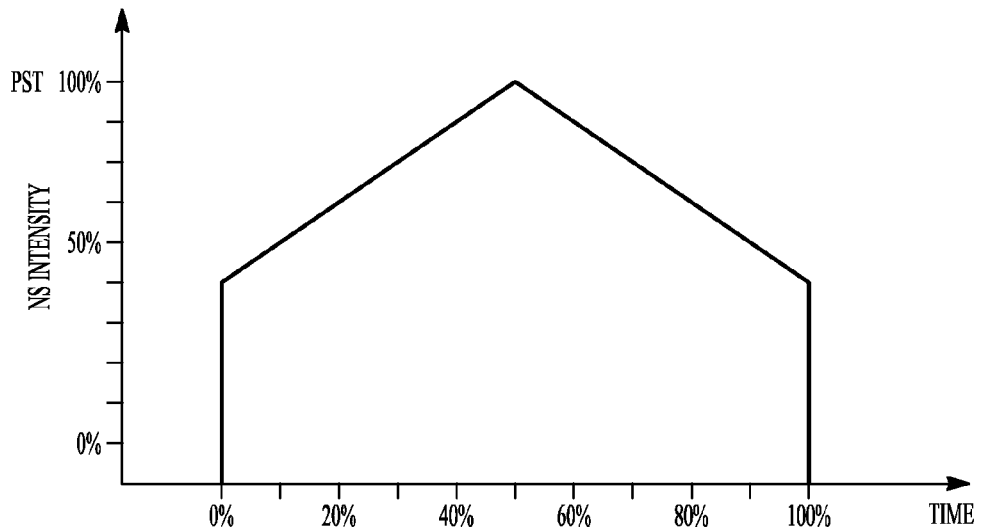
FIGS. 4 and 5 illustrate other examples of an amplitude envelopes for neural stimulation trains or duty cycles, according to various embodiments.
Figure 5:
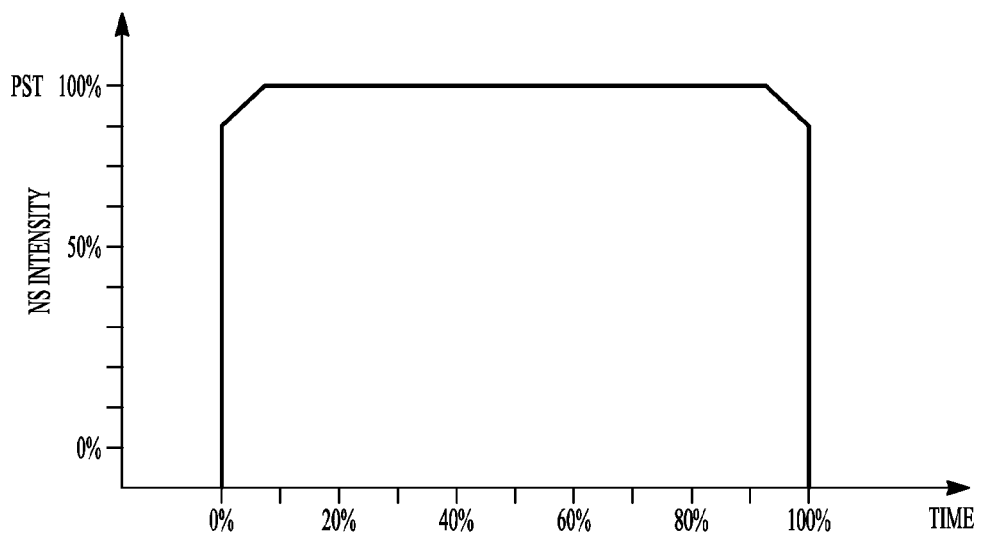

Various embodiments provide a gradual ramp up of stimulation intensity at the beginning of a duty cycle and ramp down at the conclusion of duty cycle. The ramp down of the pulse train current amplitude allows mitigation of the potential sympathetic rebound caused by baroreflex activation or respiratory reflexes. The illustrated ramp up protocol begins at a first subthreshold level 305 and ends at the PST, and the illustrated ramp down protocol begins at the PST and ends at the second subthreshold level 306, which may be but does not need to be the same as the first subthreshold level. The illustrated ramp up protocol has a duration 307 for ramping from the first subthreshold level to the PST, and the illustrated ramp down protocol has a duration 308 for ramping from the PST to the second subthreshold level. According to various embodiments, the first and second subthreshold levels can be programmed or adjusted using quantitative values or using a percentage of the threshold value. According to various embodiments, the ramp up duration and ramp down duration can be programmed or adjusted using quantitative values or using a percentage of the train duration. Various embodiments gradually increase stimulation intensity from between approximately 50% to approximately 90% of a parasympathetic stimulation threshold (PST) to a desired therapy intensity (NST LEVEL) over a period lasting from approximately 1 to approximately 15 seconds or from approximately 10% to approximately 60% of the duration of the duty cycle. Various embodiments gradually decrease stimulation intensity from the desired therapy intensity (NST LEVEL) to between approximately 50% to approximately 90% of PST over a period lasting from approximately 10% to approximately 60% of the duration of the duty cycle. The ramp up protocol and the ramp down protocol can be, but need not be, mirror images of each other. FIGS. 4 and 5 illustrate other examples of amplitude envelopes for neural stimulation trains or duty cycles, according to various embodiments. The stimulation train in FIG. 4 uses a ramp up protocol that increases stimulation from 50% of the PST to the PST for 50% of the duration of the duty cycle, and also uses a ramp down protocol that decreases stimulation from the PST to 50% of the PST for 50% of the duration of the duty cycle. The stimulation train in FIG. 5 uses a ramp up protocol that increases stimulation from 90% of the PST to the PST for 10% of the duration of the duty cycle, and also uses a ramp down protocol that decreases stimulation from the PST to 90% of the PST for 10% of the duration of the duty cycle.

The use of the non-zero subthreshold levels reduces the amount of ineffective charge (below the stimulation threshold) delivered to the neural target, thus prolonging the life of a battery in an implantable device. Also, at the leading edge of the pulse train, it is believed that the step-function in intensity from (e.g. from 0% to 50% or from 0% to 90%) increases the likelihood of capturing a higher percentage of nerve fibers.

According to some embodiments, the starting and ending intensity levels for the duty cycle and the ramp up and ramp down durations are programmed to achieve stimulation intensity at the level known to cause autonomic balance (normal parasympathetic activity). In a canine model, for example, about 82-84% of a parasympathetic bradycardia activation threshold over approximately four seconds produced the best response judged by a delta change in heart rate and mean arterial pressure and transient time. This intensity was known to result in autonomic balance. Lower intensity levels at the end of the duty cycle, for example, was demonstrated to be less effective. Possible reasons for this result include stopping parasympathetic stimulation at these levels. Additionally, subthreshold level parasympathetic stimulation can still elicit sympathetic activity in the canine.

In human patients, sympathetic rebound is expected to occur if a stimulus produces bradycardia and hypotension. A ramp down protocol can be used to limit sympathetic rebound and thus lower the potential harmful side effects of VST. Also, a ramp up protocol can be used to prevent or diminish overshoot of the desired neural response to the stimulation. The hemodynamic effects of changes in pulse train current stimulation in a canine model was shown. Electrical stimulation intensity parameters such as current (or voltage), frequency, pulse width can be gradually ramped to achieve similar effects. If neural stimulation is provided using other energy forms, the intensity of the stimulation can be adjusted by adjusting the appropriate parameters for the stimulation.

Various embodiments of the present subject matter provide a neural stimulation protocol that gradually increases neural stimulation intensity at the start of a duty cycle or stimulation pulse train. Various embodiments of the present subject matter provide a neural stimulation protocol that gradually decreases neural stimulation intensity at the end of the duty cycle or stimulation pulse train to avoid transients in the autonomic system.

Potential programmable parameters include the beginning neural stimulation intensity for the duty cycle, the ending neural stimulation intensity for the duty cycle, and the duration of the ramp up to the therapy intensity, and the duration of the ramp down from the therapy intensity, as well as the intensity level for the neural stimulation therapy.

The intensity of the electrical neural stimulation can be modulated by adjusting one or more stimulation parameters, such as amplitude, frequency, and pulse width. The adjustment can be performed as a quantitative value or as a percentage of the therapy intensity or a threshold intensity for the therapy, or as fixed time duration or a percentage of the train duration.

According to some embodiments, the neural stimulation transition protocol can be selected or programmed at the initial setup and at follow up visits. In some embodiments, the neural stimulation protocol is adjusted adaptively in an ambulatory setting based on heart rate, blood pressure, and/or a heart rate variability response at the beginning of duty cycle or pulse train and at the conclusion of the duty cycle or pulse train. Adaptation frequency can take into account circadian rhythms or be less frequent.

The present subject matter can be applied to a variety of neural stimulation therapies, including stimulation of somatic and autonomic neural targets. For example, the present subject matter can be applied to neurostimulation therapies used to treat cardiovascular diseases, such as heart failure, tachyarrhythmia, hypertension, and atherosclerosis. The present subject matter is also applicable for other neurostimulation therapies, such as functional electrical stimulation that provides more natural contractile forces, allowing for gradual increase and decrease in forceful movements. For example, the present subject matter can be implemented in a variety of prosthetics such as upper and lower extremity prosthetics, hand grasp prosthetics, hand to face movements, gate, foot drop, etc. The present subject matter can also be used in respiratory applications, such as in therapies for sleep apnea, stroke swallow, and diaphragm pacing. To assist the reader, a brief discussion of physiology and cardiovascular disorders follows, which is followed by a brief discussion of some therapies for cardiovascular disorders.

Physiology

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force is increased when the sympathetic nervous system is stimulated, and is decreased when the sympathetic nervous system is inhibited (the parasympathetic nervous system is stimulated). An afferent nerve conveys impulses toward a nerve center. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other.

Vagal modulation may be used to treat a variety of cardiovascular disorders, including heart failure, post-MI remodeling, and hypertension. These conditions are briefly described below.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Therapies

The present subject matter relates to systems, devices and methods for providing neural stimulation, such as vagus nerve stimulation, and further relates to delivering neural stimulation therapy (NST) with a ramp up intensity protocol and/or a ramp down intensity protocol. Various embodiments provide a stand-alone device, either externally or internally, to provide neural stimulation therapy. The present subject matter can be implemented in cardiac applications for neural stimulation or in non-cardiac applications for neural stimulation where a diverse nerve (such as the vagus nerve) is stimulated. For example, the present subject matter may deliver anti-remodeling therapy through neural stimulation as part of a post-MI or heart failure therapy. The present subject matter may also be implemented in non-cardiac applications, such as in therapies to treat epilepsy, depression, pain, obesity, hypertension, sleep disorders, and neuropsychiatric disorders. Various embodiments provide systems or devices that integrate neural stimulation with one or more other therapies, such as bradycardia pacing, anti-tachycardia therapy, remodeling therapy, and the like.

Neural Stimulation Therapies

Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines, for eating disorders and obesity, and for movement disorders. Many proposed neural stimulation therapies include stimulation of the vagus nerve. This listing of other neural stimulation therapies is not intended to be an exhaustive listing. Neural stimulation can be provided using electrical, acoustic, ultrasound, light, and magnetic therapies. Electrical neural stimulation can be delivered using any of a nerve cuff, intravascularly-fed lead, or transcutaneous electrodes.

A therapy embodiment involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy or ART. When delivered in conjunction with ventricular resynchronization pacing, also referred to as remodeling control therapy (RCT), such modulation of autonomic activity may act synergistically to reverse or prevent cardiac remodeling.

One neural stimulation therapy embodiment involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes (e.g. sensory nerve endings that function as a baroreceptor) that is sensitive to stretching of the wall resulting from increased pressure from within, and that functions as the receptor of the central reflex mechanism that tends to reduce that pressure. Baroreflex neural targets also include neural pathways extending from the baroreceptors. Baroreflex neural targets can be found in the wall of the auricles of the heart, cardiac fat pads, vena cava, aortic arch and carotid sinus. Examples of afferent nerve trunks that can serve as baroreflex neural targets include the vagus, aortic and carotid nerves. Stimulating baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of the arterial wall. Some aspects of the present subject matter locally stimulate specific nerve endings in arterial walls rather than stimulate afferent nerve trunks in an effort to stimulate a desired response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the chambers of the heart, the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Neural stimulation (e.g. sympathetic nerve stimulation and/or parasympathetic nerve inhibition) can mimic the effects of physical conditioning. It is generally accepted that physical activity and fitness improve health and reduce mortality. Studies have indicated that aerobic training improves cardiac autonomic regulation, reduces heart rate and is associated with increased cardiac vagal outflow. A baseline measurement of higher parasympathetic activity is associated with improved aerobic fitness. Exercise training intermittently stresses the system and increases the sympathetic activity during the stress. However, when an exercise session ends and the stress is removed, the body rebounds in a manner that increases baseline parasympathetic activity and reduces baseline sympathetic activity. Physical conditioning can be considered to be a repetitive, high-level exercise that occurs intermittently over time.

Physical conditioning therapy can be applied as therapy for heart failure. Examples of other physical conditioning therapies include therapies for patients who are unable to exercise. For example, physical conditioning using sympathetic stimulation/parasympathetic inhibition for a bed-bound, post-surgical patient in a hospital may enable the patient to maintain strength and endurance until such time that the patient is able to exercise again. By way of another example, a morbidly obese patient may be unable to exercise, but may still benefit from the physical conditioning therapy. Furthermore, patients with injuries such as joint injuries that prevent them from performing their normal physical activities may benefit from the physical conditioning therapy.

Myocardial Stimulation Therapies

Various neural stimulation therapies can be integrated with various myocardial stimulation therapies. The integration of therapies may have a synergistic effect. Therapies can be synchronized with each other, and sensed data can be shared between the therapies. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Device Embodiments

Figure 6:
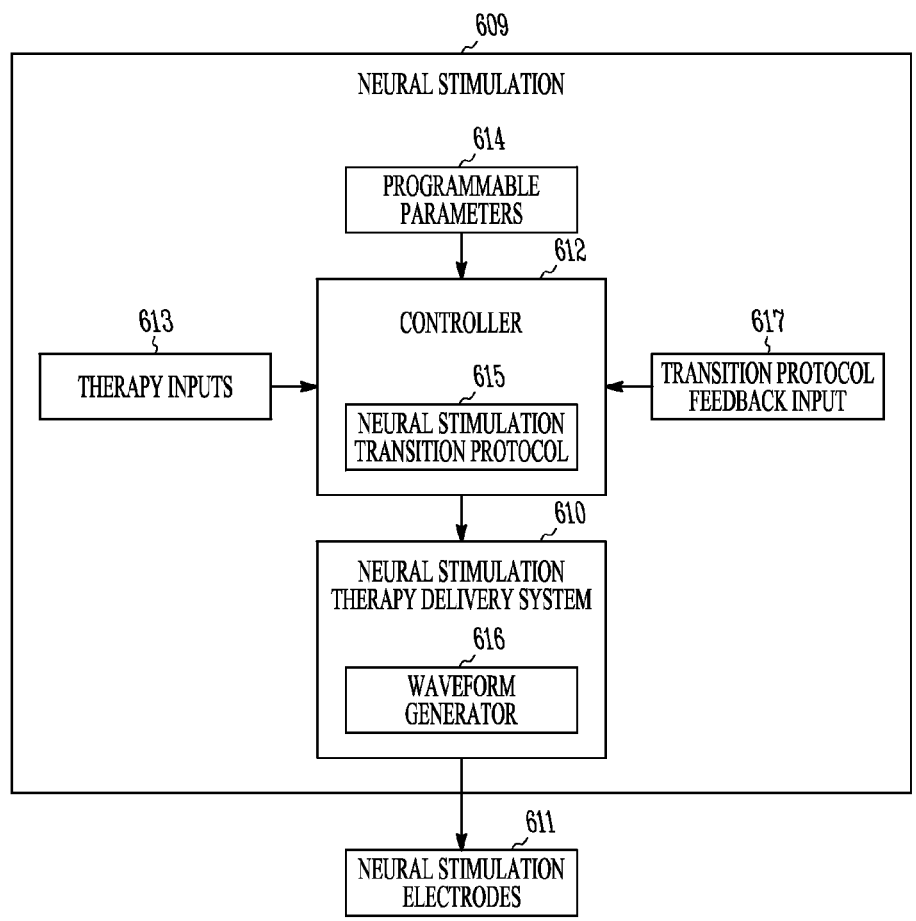
FIG. 6 illustrates a neural stimulator device embodiment adapted to deliver intermittent neural stimulation therapy using a ramp up intensity protocol and/or a ramp down intensity protocol, according to various embodiments.

FIG. 6 illustrates a neural stimulator device embodiment adapted to deliver intermittent neural stimulation therapy using a ramp up intensity protocol and/or a ramp down intensity protocol, according to various embodiments. The illustrated device 609 can be an implantable device or an external device. The illustrated device includes a neural stimulation delivery system 610 adapted to deliver a neural stimulation signal to the neural stimulation electrode(s) or transducer(s) 611 to deliver the neural stimulation therapy. Examples of neural stimulation electrodes include nerve cuff electrodes, intravascularly placed electrodes, and transcutaneous electrodes. Examples of neural stimulation transducers includes ultrasound, light and magnetic energy transducers. A controller 612 receives therapy inputs 613, and appropriately controls the neural stimulation therapy delivery system 610 using the therapy inputs 613 to provide the appropriate neural stimulation signal to the electrode(s)/transducer(s) that results in a desired intensity of neural stimulation. The illustrated device includes a memory 614 to store programmable parameters. The controller 612 implements a transition protocol 615 using the programmable parameters to control the waveform generator 616 of the neural stimulation therapy delivery system 610. Examples of programmable parameters, any one or more of which can be stored in the memory 614, include a starting subthreshold intensity value, an ending intensity subthreshold value, a ramp up duration, a ramp down duration, and further includes a neural stimulation intensity and/or a threshold. The illustrated device includes a transition protocol feedback input 617. The input can receive a communication from a device programmer, for use by a physician or patient in changing the programmable parameters based on observed conditions. The input can receive a feedback from physiologic sensors used to monitor transient responses at the beginning and/or end of the neural stimulation train. Examples of such sensors used to provide feedback for the transition protocol include heart rate and blood pressure sensors.

Advanced patient management systems can be used to enable the patient and/or doctor to adjust parameter(s) to compensate for undesired transient responses, such as may be sensed by physiologic parameters and output to the patient and/or doctor. The inputs can be provided by computers, programmers, cell phones, personal digital assistants, and the like. The patient can call a call center using a regular telephone, a mobile phone, or the internet. The communication can be through a repeater, similar to that used in Guidant's Latitude patient management system. In response, the call center (e.g. server in call center) can automatically send information to the device to adjust or titrate the therapy. The call center can inform the patient's physician of the event. A device interrogation can be automatically triggered. The results of the device interrogation can be used to determine if and how the therapy should be adjusted and/or titrated to improve the transient response. A server can automatically adjust and/or titrate the therapy using the results of the device interrogation. Medical staff can review the results of the device interrogation, and program the device through the remote server to provide the desired therapy adjustments and/or titrations. The server can communicate results of the device interrogation to the patient's physician, who can provide input or direction for adjusting and/or titrating the therapy.

Figure 7:
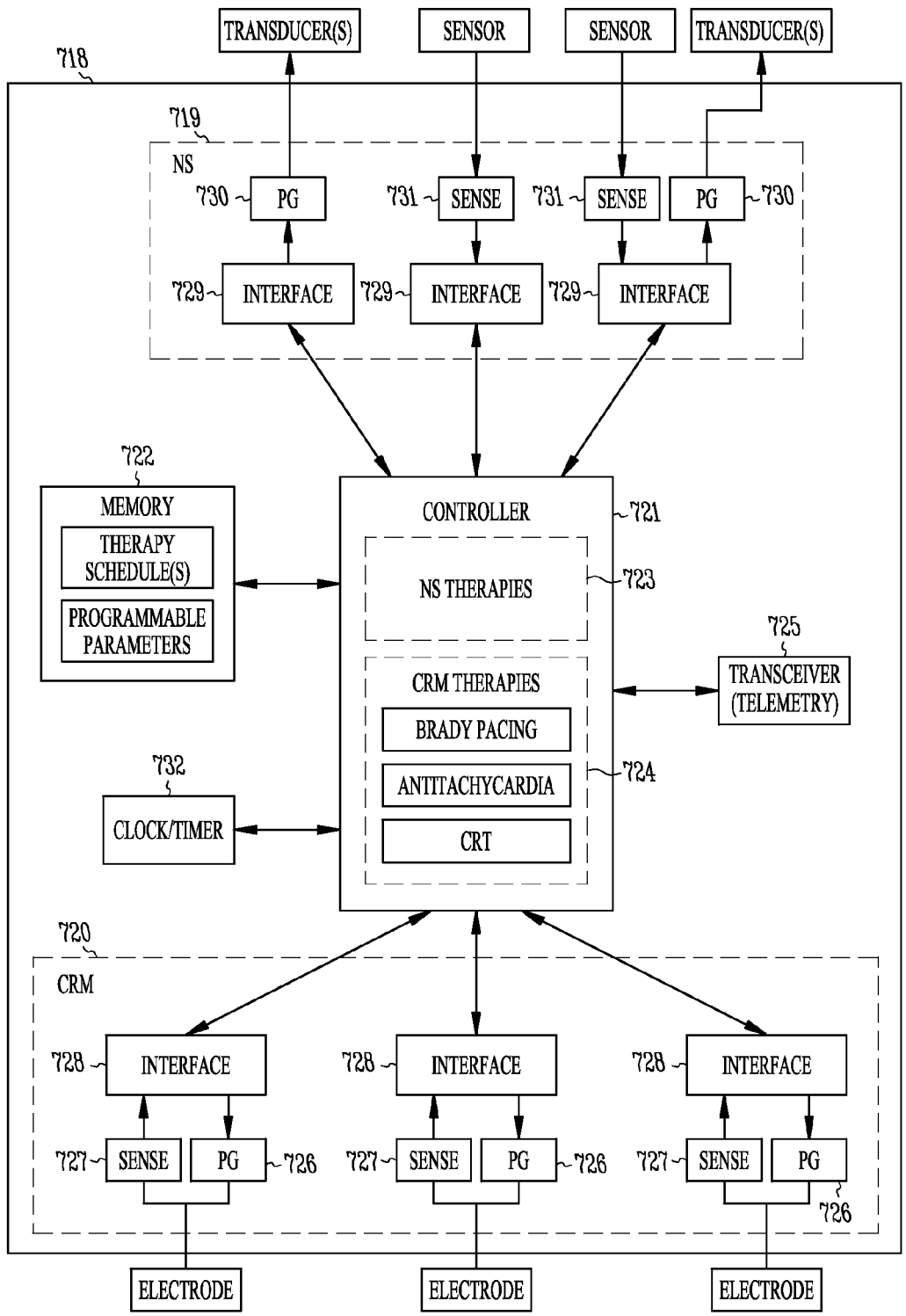
FIG. 7 illustrates an implantable medical device (IMD) having a neural stimulation (NS) component and a cardiac rhythm management (CRM) component, according to various embodiments of the present subject matter.

FIG. 7 illustrates an implantable medical device (IMD) 718 having a neural stimulation (NS) component 719 and a cardiac rhythm management (CRM) component 720 according to various embodiments of the present subject matter. The illustrated device includes a controller 721 and memory 722. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy 723 can include any neural stimulation therapy, such as a therapy for ventricular remodeling. Various embodiments include CRM therapies 724, such as bradycardia pacing, anti-tachycardia therapies such as ATP, defibrillation and cardioversion, and cardiac resynchronization therapy (CRT). The illustrated device further includes a transceiver 725 and associated circuitry for use to communicate with a programmer or another external or internal device. Various embodiments include a telemetry coil.

The CRM therapy section 720 includes components, under the control of the controller, to stimulate a heart and/or sense cardiac signals using one or more electrodes. The illustrated CRM therapy section includes a pulse generator 726 for use to provide an electrical signal through an electrode to stimulate a heart, and further includes sense circuitry 727 to detect and process sensed cardiac signals. An interface 728 is generally illustrated for use to communicate between the controller 721 and the pulse generator 726 and sense circuitry 727. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 719 includes components, under the control of the controller, to stimulate a neural stimulation target and/or sense parameters associated with nerve activity or surrogates of nerve activity such as blood pressure and respiration. Three interfaces 729 are illustrated for use to provide neural stimulation. However, the present subject matter is not limited to a particular number interfaces, or to any particular stimulating or sensing functions. Pulse generators 730 are used to provide electrical pulses to transducer or transducers for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 731 are used to detect and process signals from a sensor, such as a sensor of nerve activity, blood pressure, respiration, and the like. The interfaces 729 are generally illustrated for use to communicate between the controller 721 and the pulse generator 730 and sense circuitry 731. Each interface, for example, may be used to control a separate lead. Various embodiments of the NS therapy section only includes a pulse generator to stimulate a neural target. The illustrated device further includes a clock/timer 732, which can be used to deliver the programmed therapy according to a programmed stimulation protocol and/or schedule.

Figure 8:
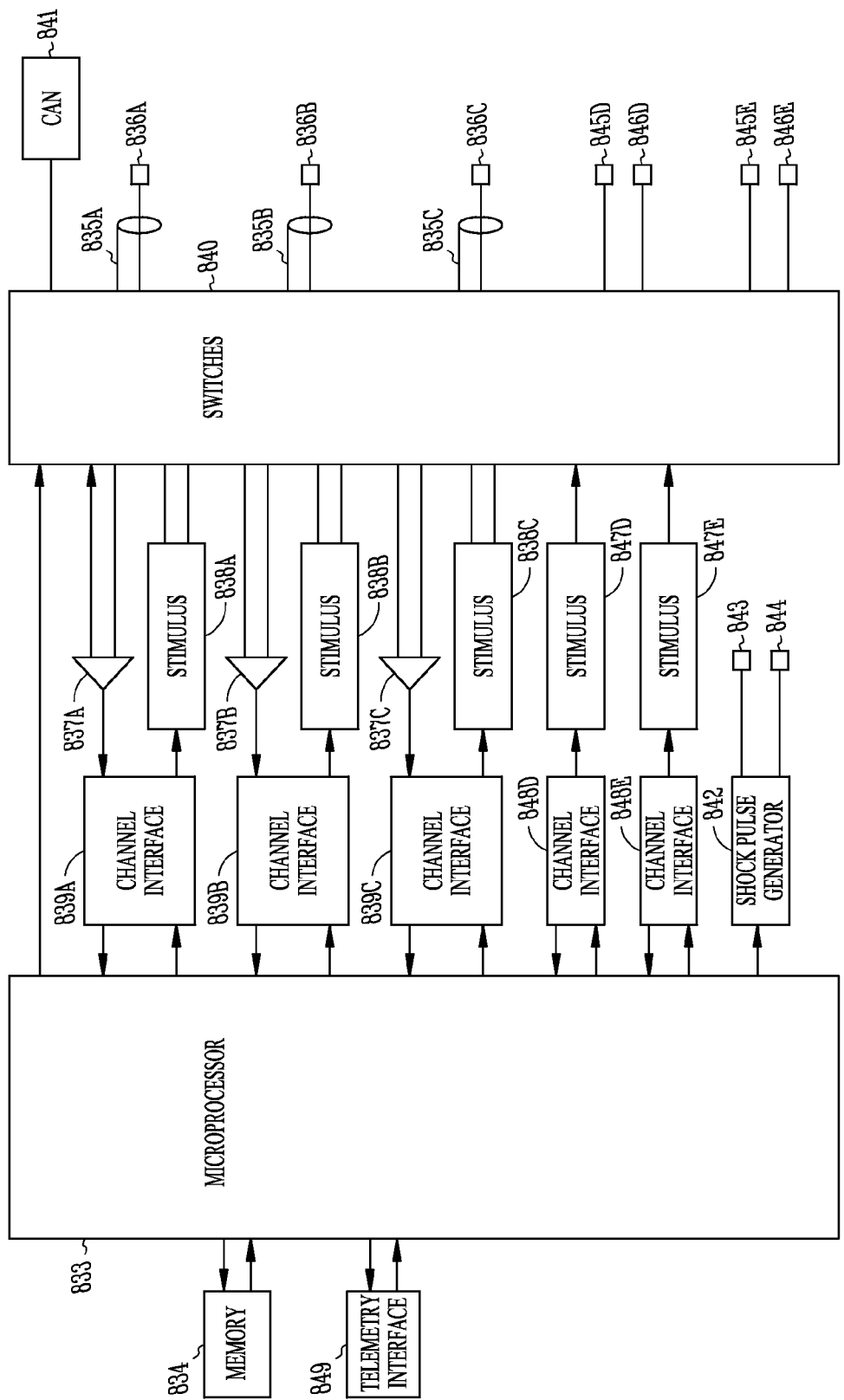
FIG. 8 illustrates a system diagram of an embodiment of a microprocessor-based implantable device, according to various embodiments.

FIG. 8 shows a system diagram of an embodiment of a microprocessor-based implantable device, according to various embodiments. The controller of the device is a microprocessor 833 which communicates with a memory 834 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 835A-C and tip electrodes 836A-C, sensing amplifiers 837A-C, pulse generators 838A-C, and channel interfaces 839A-C. Each channel thus includes a pacing channel made up of the pulse generator connected to the electrode and a sensing channel made up of the sense amplifier connected to the electrode. The channel interfaces 839A-C communicate bidirectionally with the microprocessor 833, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 840 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 841 or an electrode on another lead serving as a ground electrode. A shock pulse generator 842 is also interfaced to the controller for delivering a defibrillation shock via shock electrodes 843 and 844 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 845D and a second electrode 846D, a pulse generator 847D, and a channel interface 848D, and the other channel includes a bipolar lead with a first electrode 845E and a second electrode 846E, a pulse generator 847E, and a channel interface 848E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 849 connected to the microprocessor, which can be used to communicate with an external device. The illustrated microprocessor 833 is capable of performing neural stimulation therapy routines and myocardial (CRM) stimulation routines. Examples of NS therapy routines include a therapies to provide physical conditioning and therapies to treat ventricular remodeling, hypertension, sleep disordered breathing, blood pressure control such as to treat hypertension, cardiac rhythm management, myocardial infarction and ischemia, heart failure, epilepsy, depression, for pain, migraines, eating disorders and obesity, and movement disorders. The present subject matter is not limited to a particular neural stimulation therapy. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

System Embodiments

Figure 9:
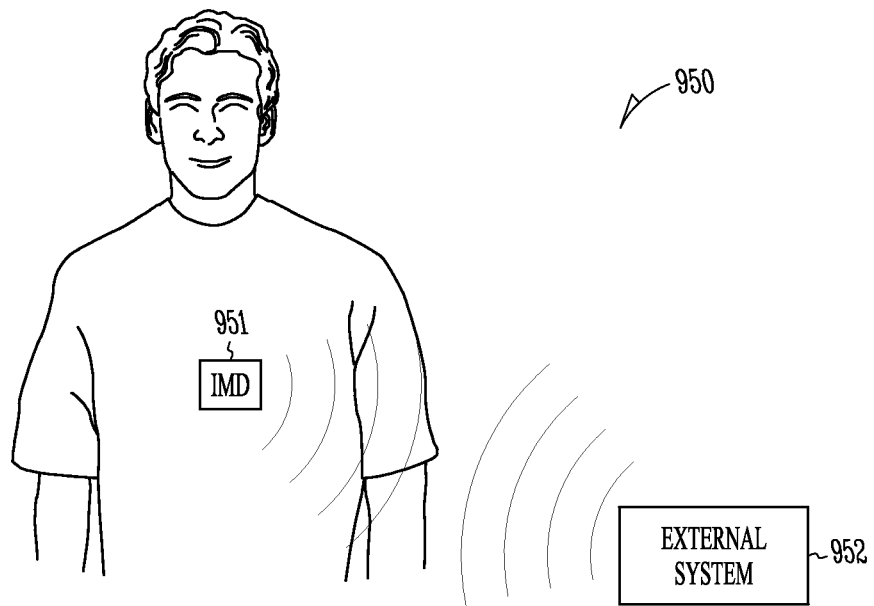
FIG. 9 illustrates a system including an implantable medical device (IMD) and an external system or device, according to various embodiments of the present subject matter.

FIG. 9 illustrates a system 950 including an implantable medical device (IMD) 951 and an external system or device 952, according to various embodiments of the present subject matter. Various embodiments of the IMD include NS functions or include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target using a stimulation protocol that includes intermittent neural stimulation with a ramp up intensity or a ramp down intensity to avoid or diminish undesired transient responses from intermittent neural stimulation. For example, an embodiment delivers vagus nerve stimulation and avoids or diminishes coughs attributable to the neural stimulation.

The external system allows a user such as a physician or other caregiver or a patient to control the operation of the IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 10:
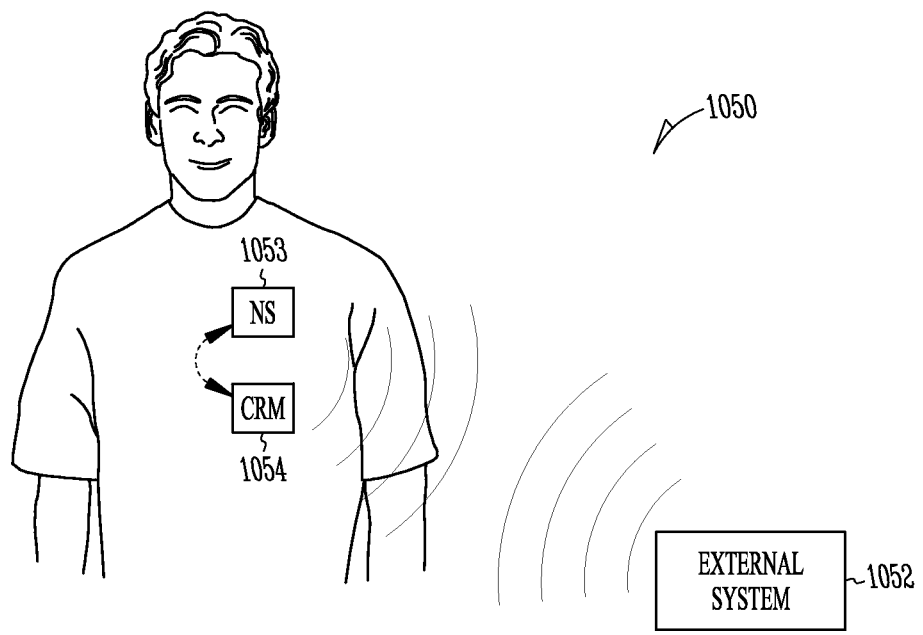
FIG. 10 illustrates a system including an external device, an implantable neural stimulator (NS) device and an implantable cardiac rhythm management (CRM) device, according to various embodiments of the present subject matter.

FIG. 10 illustrates a system 1050 including an external device 1052, an implantable neural stimulator (NS) device 1053 and an implantable cardiac rhythm management (CRM) device 1054, according to various embodiments of the present subject matter. Various aspects involve a method for communicating between an NS device and a CRM device or other cardiac stimulator. In various embodiments, this communication allows one of the devices 1053 or 1054 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

FIGS. 11-14 illustrate system embodiments adapted to provide vagal stimulation, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve.

Figure 11:
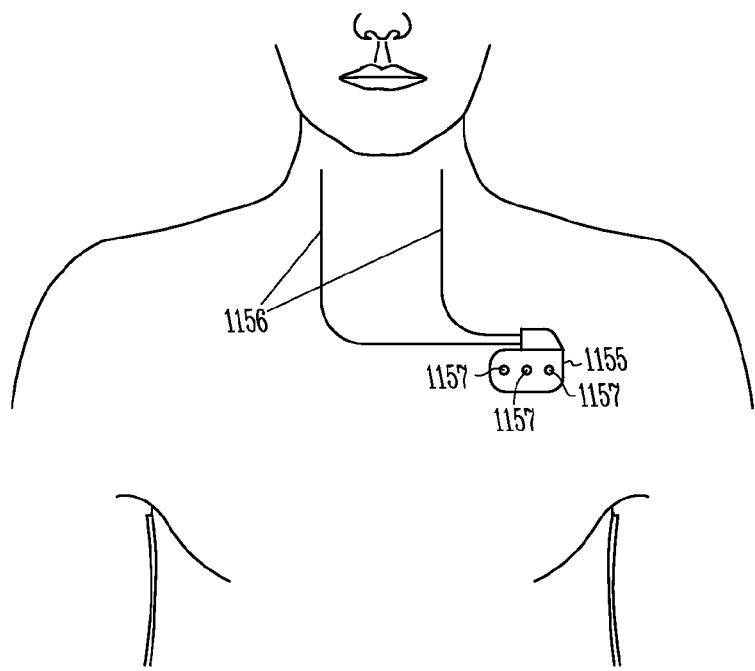
FIG. 11 illustrates a system embodiment in which an IMD is placed subcutaneously or submuscularly in a patient's chest with lead(s) positioned to stimulate a vagus nerve.

FIG. 11 illustrates a system embodiment in which an IMD 1155 is placed subcutaneously or submuscularly in a patient's chest with lead(s) 1156 positioned to stimulate a vagus nerve. According to various embodiments, neural stimulation lead(s) 1156 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes 1157 on the housing of the device. These ECG electrodes are capable of being used to detect heart rate, for example.

Figure 12:
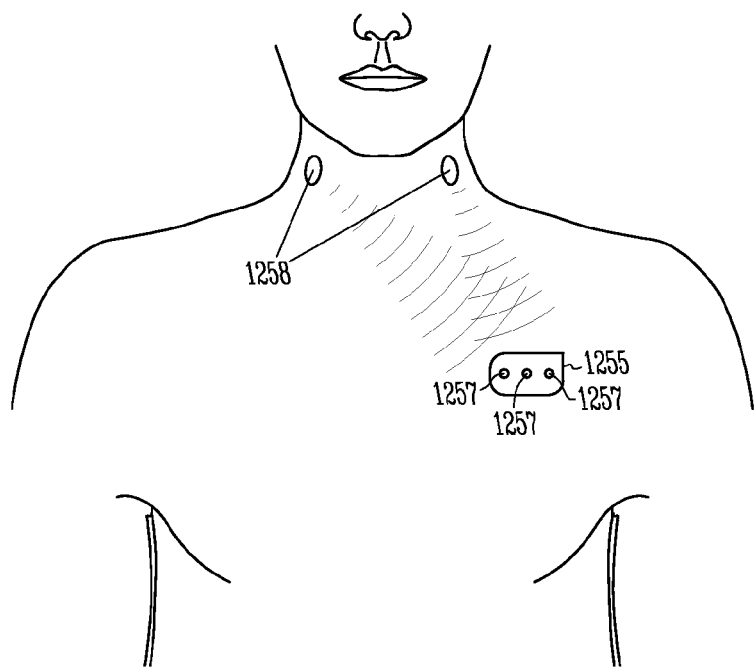
FIG. 12 illustrates a system embodiment that includes an implantable medical device (IMD) with satellite electrode(s) positioned to stimulate at least one neural target.

FIG. 12 illustrates a system embodiment that includes an implantable medical device (IMD) 1255 with satellite electrode(s) 1258 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 1257 are capable of being used to detect heart rate, for example.

Figure 13:
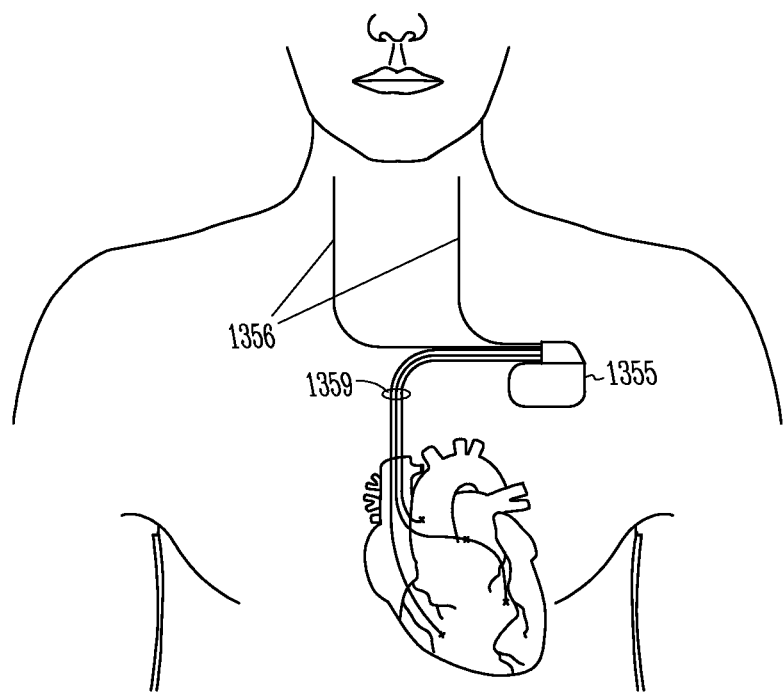
FIG. 13 illustrates an IMD placed subcutaneously or submuscularly in a patient's chest with lead(s) positioned to provide a CRM therapy to a heart, and with lead(s) positioned to stimulate and/or inhibit neural traffic at a neural target, such as a vagus nerve, according to various embodiments.

FIG. 13 illustrates an IMD 1355 placed subcutaneously or submuscularly in a patient's chest with lead(s) 1359 positioned to provide a CRM therapy to a heart, and with lead(s) 1356 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 14:
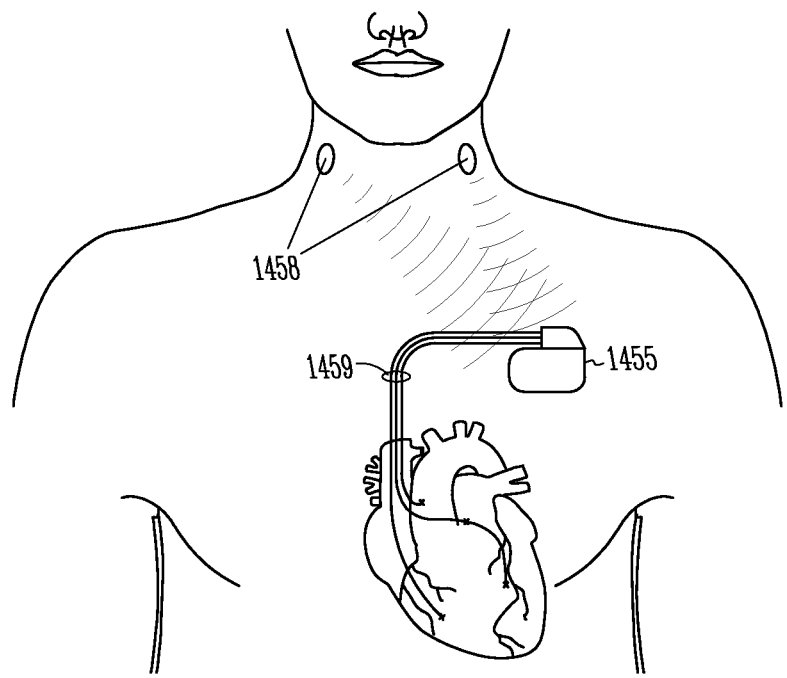
FIG. 14 illustrates an IMD with lead(s) positioned to provide a CRM therapy to a heart, and with satellite transducers positioned to stimulate/inhibit a neural target such as a vagus nerve, according to various embodiments.

FIG. 14 illustrates an IMD 1455 with lead(s) 1459 positioned to provide a CRM therapy to a heart, and with satellite transducers 1458 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 15:
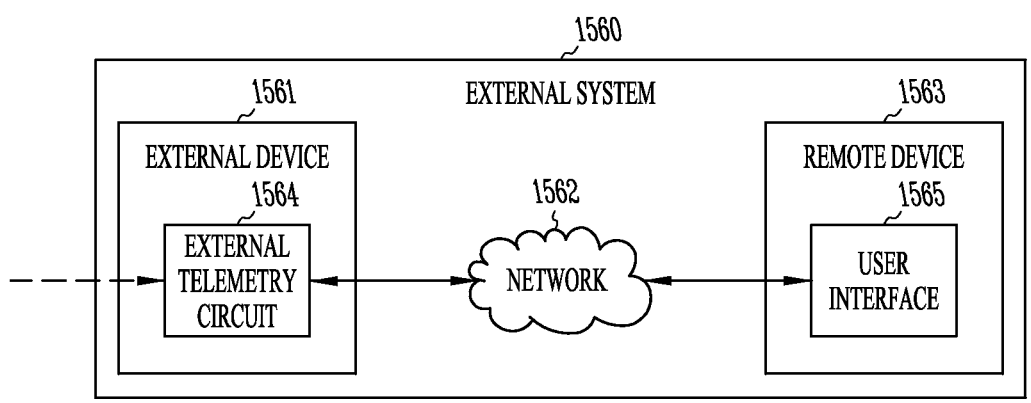
FIG. 15 is a block diagram illustrating an embodiment of an external system.

FIG. 15 is a block diagram illustrating an embodiment of an external system 1560. The external system includes a programmer, in some embodiments. In the illustrated embodiment, the external system includes a patient management system. As illustrated, the external system 1560 is a patient management system including an external device 1561, a telecommunication network 1562, and a remote device 1563. The external device 1561 is placed within the vicinity of an implantable medical device (IMD) and includes an external telemetry system 1564 to communicate with the IMD. The remote device(s) 1563 is in one or more remote locations and communicates with the external device 1561 through the network 1562, thus allowing a physician or other caregiver to monitor and treat a patient from a distant location and/or allowing access to various treatment resources from the one or more remote locations. The illustrated remote device 1563 includes a user interface 1565. According to various embodiments, the external device 1561 includes a neural stimulator, a programmer or other device such as a computer, a personal data assistant or phone. The external device 1561, in various embodiments, includes two devices adapted to communicate with each other over an appropriate communication channel, such as a computer by way of example and not limitation. The external device can be used by the patient or physician to provide side effect feedback indicative of patient discomfort, for example.

According to various embodiments, the device, as illustrated and described above, is adapted to deliver neural stimulation as electrical stimulation to desired neural targets, such as through one or more stimulation electrodes positioned at predetermined location(s). Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by a processor cause the processor to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:
1. A method, comprising:
generating a neural stimulation signal only during a duty cycle of a stimulation period to provide intermittent neural stimulation for a neural stimulation therapy, including:
generating the neural stimulation signal during the duty cycle of the stimulation period to provide the neural stimulation therapy with an intensity at a therapy level for a portion of the duty cycle, the neural stimulation signal including a stimulation pulse train; and
implementing a ramp up protocol to begin the duty cycle, a ramp down protocol to end the duty cycle, or both the ramp up protocol to begin the duty cycle and the ramp down protocol to end the duty cycle;

wherein the ramp up protocol includes a programmed value for at least one programmable ramp up parameter, and wherein implementing the ramp up protocol includes stepping up the intensity from a zero value before the duty cycle when the neural stimulation signal is not generated to a non-zero first subthreshold level for the neural stimulation therapy at the beginning of the duty cycle, and implementing a programmed ramp up algorithm to ramp up the intensity from the non-zero first subthreshold level at the beginning of the duty cycle to the therapy level; and wherein the ramp down protocol includes a programmed value for at least one programmable ramp down parameter, and wherein implementing the ramp down protocol includes implementing a programmed ramp down algorithm to ramp down the intensity from the therapy level to a non-zero second subthreshold level for the neural stimulation therapy at the end of the duty cycle, and stepping down the neural stimulation intensity from the non-zero second subthreshold level at the end of the duty cycle to the zero value after the duty cycle.

2. The method of claim 1, wherein implementing the ramp up protocol or the ramp down protocol includes changing at least one of an amplitude, a frequency, or a pulse width of the stimulation pulse train.

3. The method of claim 1, further comprising stimulating at least one of an autonomic neural target using the neural stimulation signal, the autonomic neural target including a vagus nerve, a cardiac nerve, or a cardiac fat pad, wherein implementing the ramp up protocol or the ramp down protocol includes avoiding or reducing overshoot or rebound of a target autonomic response.

4. The method of claim 1, further comprising:
monitoring a physiologic response at the beginning or the end of the duty cycle; and
automatically adjusting according to the monitored physiologic response the at least one programmable ramp up parameter, the at least one programmable ramp up parameter, or both the at least one programmable ramp up parameter and the at least one programmable ramp up parameter, wherein:
the monitored physiologic response includes a heart rate response, a blood pressure response, or a heart rate variability response;
the at least one programmable ramp up parameter includes a non-zero first sub-threshold level parameter, a ramp up duration parameter, or a therapy level intensity parameter; and
the at least one programmable ramp down parameter includes the therapy level intensity parameter, a non-zeros second subthreshold level parameter, or a ramp-down duration parameter.

5. The method of claim 4, wherein the heart rate response includes a change in heart rate or an acceleration of heart rate, and wherein the blood pressure response includes a change in mean blood pressure, or an acceleration of mean blood pressure.

6. The method of claim 4, wherein automatically adjusting according to the monitored physiologic response the at least one programmable ramp up parameter or the at least one programmable ramp down parameter further includes:
programming the therapy level intensity parameter to a desired therapy intensity according to the monitored heart rate response or the monitored blood pressure response; and programming the first subthreshold level parameter or the second subthreshold level parameter to a percentage of the programmed therapy level intensity.

7. The method of claim 6, wherein the percentage is between approximately 50% to approximately 90%.

8. The method of claim 4, wherein automatically adjusting according to the monitored physiologic response the at least one programmable ramp up parameter or the programmable ramp down parameter further includes adjusting the ramp up duration parameter or the ramp down duration parameter in adaptation to the monitored physiologic response and a desired physiological response to the neural stimulation.

9. The method of claim 8, wherein the adjusted ramp up duration parameter or the adjusted ramp down duration parameter is within a range between approximately 1 to approximately 15 seconds or between approximately 10% to approximately 60% of the duration of the duty cycle.

10. The method of claim 1, further comprising detecting a circadian rhythm and adjusting according to the detected circadian rhythm the at least one programmable ramp up parameter or the programmable ramp down parameter.

11. A neural stimulator, comprising:
a neural stimulation delivery system configured to generate a neural stimulation signal only during a duty cycle of a stimulation period to provide intermittent neural stimulation for a neural stimulation therapy; and
a controller configured to control the neural stimulation delivery system using at least one programmable parameter to:
generate the neural stimulation signal during the duty cycle of the stimulation period to provide the neural stimulation therapy with an intensity at a therapy level for a portion of the duty cycle, the neural stimulation signal including a stimulation pulse train; and
implement a protocol selected from the group of protocols consisting of:
a ramp up protocol to begin the duty cycle by stepping up the intensity from a zero value before the duty cycle when the neural stimulation signal is not generated to a non-zero first subthreshold level for the neural stimulation therapy at the beginning of the duty cycle, and the ramp up protocol further including a programmed ramp up algorithm to ramp up the intensity from the non-zero first subthreshold level at the beginning of the duty cycle to the therapy level;
a ramp down protocol, including a programmed ramp down algorithm to ramp down the intensity from the therapy level and ending with a non-zero second subthreshold level for the neural stimulation therapy at the end of the duty cycle, and the ramp down protocol further including stepping down the neural stimulation intensity from the non-zero second subthreshold level at the end of the duty cycle to the zero value after the duty cycle; and
a protocol that includes both the ramp up protocol to begin the duty cycle and the ramp down protocol to end the duty cycle.

12. The stimulator of claim 11, wherein in implementing the ramp up protocol or the ramp down protocol the controller is configured to change at least one of an amplitude, a frequency, or a pulse width of the stimulation pulse train.

13. The stimulator of claim 11, further comprising a physiologic sensor configured to sense a physiologic response at the beginning or the end of the duty cycle, wherein:

the physiologic sensor includes at least one of a heart rate sensor, a blood pressure sensor, or a heart rate variability sensor; and the controller is configured to use the send physiologic response to automatically adjust the at least one programmable parameter selected from a group of parameters consisting of: a non-zero first sub-threshold level parameter; a ramp up duration parameter; a therapy level intensity parameter; a non-zero second subthreshold level parameter; and a ramp-down duration parameter.

14. The stimulator of claim 13, wherein the controller is further configured to:

use the sensed heart rate response or the sensed blood pressure response to program the therapy level intensity parameter to a desired therapy intensity; and program the first subthreshold level parameter or the second subthreshold level parameter to a percentage of the determined therapy level intensity.

15. The stimulator of claim 13, wherein the controller is configured to adjust the ramp up duration parameter or the ramp down duration parameter in adaptation to the sensed physiologic response and a desired physiological response to the neural stimulation.

16. The stimulator of claim 15, wherein the controller is further configured to maintain the adjusted ramp up duration parameter or the adjusted ramp down duration parameter within a predetermined duration range.

17. The stimulator of claim 11, further comprising a circadian rhythm detector configured to detect a circadian rhythm, wherein the controller is configured to use the detected circadian rhythm to automatically adjust the at least one programmable parameter for the ramp up protocol, the ramp down protocol or both the ramp up and ramp down protocols.

18. The stimulator of claim 11, wherein the neural stimulation delivery system is configured to stimulate an autonomic neural target including a vagus nerve, a cardiac nerve, or a cardiac fat pad.

19. The stimulator of claim 18, wherein the neural stimulation delivery system is configured to stimulate an intravascular site proximate to the autonomic neural target.

20. The stimulator of claim 11, further comprising a cardiac pacing system, wherein:

the stimulator is an implantable stimulator configured to generate the neural stimulation signal for heart failure therapy; and the cardiac pacing system includes an implantable pulse generator configured to generate cardiac resynchronization pacing for heart failure therapy.

* * * * *